United States Patent [19]

Humphreys

[11] Patent Number: 4,786,812
[45] Date of Patent: Nov. 22, 1988

[54] PORTABLE GERMICIDAL ULTRAVIOLET LAMP

[75] Inventor: Wesley G. Humphreys, Huntingdon Valley, Pa.

[73] Assignee: Dora DiCamillo 1988 Trust, Newtown, Pa.

[21] Appl. No.: 935,794

[22] Filed: Nov. 28, 1986

[51] Int. Cl.⁴ .............................................. G01N 23/00
[52] U.S. Cl. ..................................... 250/455.1; 422/24
[58] Field of Search .......................... 250/455.1, 492.1; 128/396; 422/24

[56] References Cited

U.S. PATENT DOCUMENTS

| | | | |
|---|---|---|---|
| 2,248,618 | 7/1941 | Fischer | 422/24 |
| 2,265,252 | 12/1941 | Schaefer | 422/24 |
| 2,350,665 | 6/1944 | Alexander | 422/24 |
| 2,654,021 | 9/1953 | Bartholomew | 422/24 |
| 2,732,501 | 1/1956 | Blaeker | 422/24 |
| 3,107,863 | 10/1963 | Potapenko | 422/24 |
| 3,107,974 | 10/1963 | Potapenko | 422/24 |
| 3,518,046 | 6/1970 | Cicirello | 422/24 |
| 4,210,429 | 7/1980 | Golstein | 422/24 |

FOREIGN PATENT DOCUMENTS

| | | | |
|---|---|---|---|
| 2732859 | 2/1979 | Fed. Rep. of Germany | 422/24 |
| 2307547 | 2/1976 | France | 422/24 |

Primary Examiner—Bruce C. Anderson
Attorney, Agent, or Firm—John W. Logan, Jr.

[57] ABSTRACT

A lightweight and portable germ killing machine is disclosed. The machine has a plurality of ultraviolet light bulbs fixed inside of a protective, and light-shielding, housing, and adjacent to a reflective surface with air passageways therein. A fan is located above the reflective surface and draws air from around the housing towards, and around, the lightbulbs thereby killing any germs floating therein. Filters are located along the sides and underside to block out potentially damaging items.

10 Claims, 5 Drawing Sheets

IX-A

PORTABLE GERMICIDAL ULTRAVIOLET LAMP

BACKGROUND OF THE INVENTION

It has been found that bacteria or other microorganisms, including mold spores, yeast and virus, can be destroyed in the air or on exposed surfaces if they are subjected to ultraviolet light with a wavelength of 253.7 nanometers. Research performed by Dr. Harvey C. Rentschler of Westinghouse Laboratories in the early 1930's led to the development of the Sterilamp ® Ultraviolet Tube, which tube emits UV light with that wavelength, and that tube is in use today. In order for the UV light from these tubes to kill microorganisms, the rays must directly strike them. The exposure to UV light necessary to kill bacteria (or the "kill" factor) is a product of time and intensity. If the bacteria or mold spores are hidden below the surface of a material or are not in the direct path of the rays, they will not be destroyed. Because of the absolute necessity for antiseptic surroundings, tubes that emit light of the required wavelength are often used in operating rooms, wards and nurseries of hospitals, and, as used today, are fixed to walls or ceilings.

There is a danger to humans though, from use of UV light, that heretofore has hampered widespread application of the principles of UV cleanliness: radiation sickness. This manifests itself as a reddening of the skin or an irritation of the eyes if there is prolonged, or intense, exposure to the rays. For this reason, lights fixed to ceilings or walls must be shielded to prevent direct or reflected UV light from striking humans. This type of stationary and shielded light fixture is therefore only partially effective in destroying microorganisms because there are many surfaces, and hidden areas, where the UV light rays cannot reach and because it is necessary to affix the UV light to a place on the wall that necessarily limits their effective "kill" factor.

The instant invention is the first of its kind to enable all businesses, such as hospitals, medical clinics, food processing centers, to name a few, concerned with cleaning bacteria and other microorganisms to have a portable germicidal machine that utilizes this specific UV light. The UV lamp of the present invention not only kills these germs on the surface below or alongside, but also pulls or draws germs from out of carpets or crevices, such as corners between a wall and a floor.

SUMMARY OF THE INVENTION

A lightweight and portable germ-killing machine is disclosed that uses a plurality of ultraviolet light bulbs that give off light with a wavelength in the region of 253.7 nanometers. The machine has protective sides with movable vents around the light bulbs to shield direct light from human sight, a reflective surface with air passages therein located above the bulbs, sliding means attached on the underside to facilitate easy movement and a fan located above the bulbs to draw air and germs up from a carpet or other surface past the bulbs to effectuate a very high rate of germ destruction as the machine is moved over a surface. Filters located on the underside and in each side prevent potentially damaging items from being drawn in by the fan. In an alternate embodiment, the machine has attachments to flush out with air streams, for intake by the fan-directed currents, germs hidden behind objects.

OBJECTS OF THE INVENTION

It is an object of the present invention to provide a lightweight and portable machine that kills germs on any surface by shining ultraviolet light thereon.

It is a further object of the present invention to provide a portable and lightweight machine that uses an internal fan to draw germs floating in room air into direct UV light from germ-killing ultraviolet bulbs.

It is a still further object of the present invention to provide a portable and lightweight machine that produces air currents that can be used to flush germs from behind objects out into room currents.

These and other objects and many attendant advantages of the present invention will be readily appreciated as the same become better understood by reference to the following detailed description when considered in connection with the accompanying drawings.

DETAILED DESCRIPTION OF THE PREFERRED EMBODIMENT

Figures 1, 2:
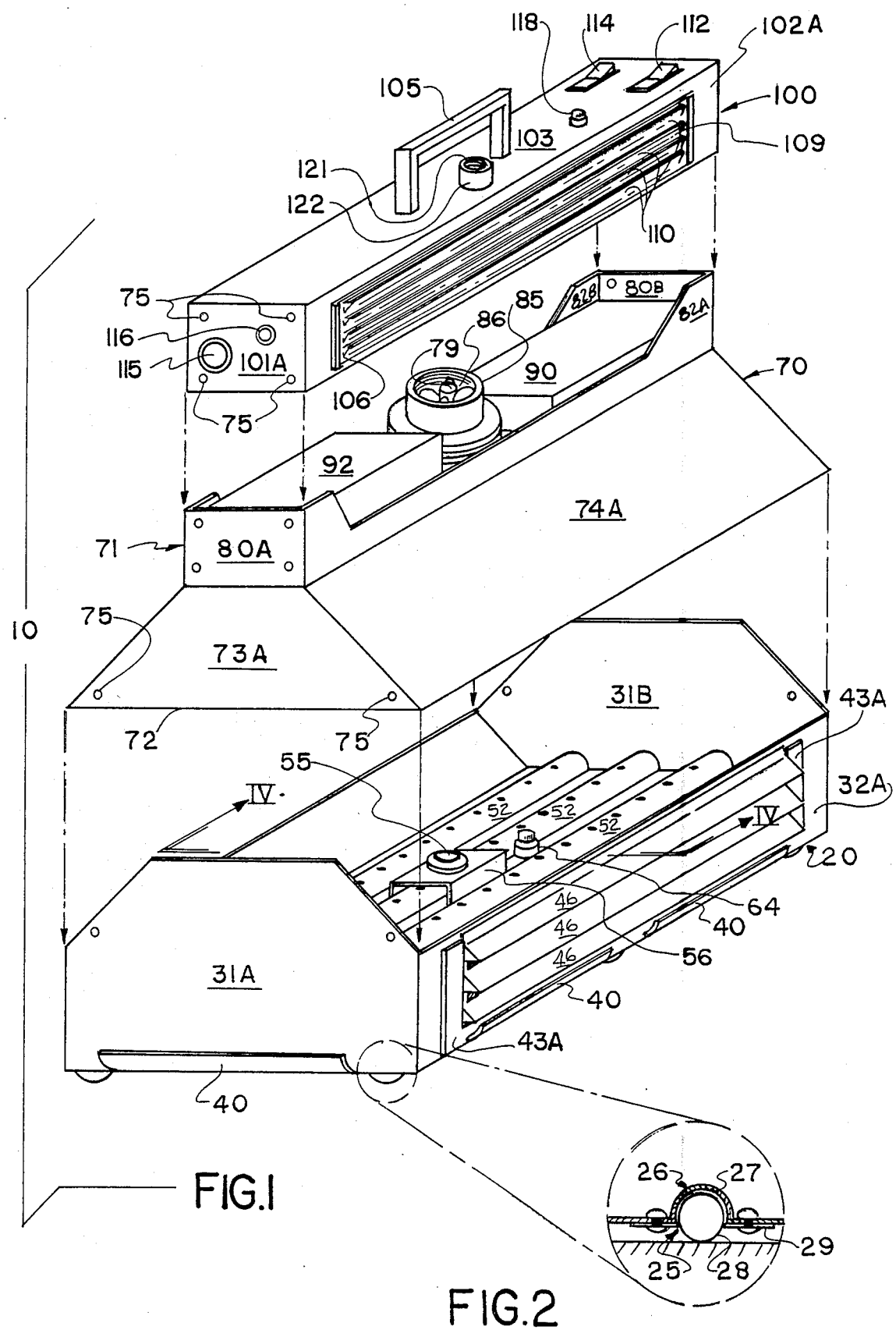
FIG. 1 shows an expanded perspective view of A Portable Germicidal Ultraviolet Lamp.
FIG. 2 shows a fragmented, end elevation view of a roller assembly 25 in base module 20 with end piece 31A cut away.
Figures 5, 6:
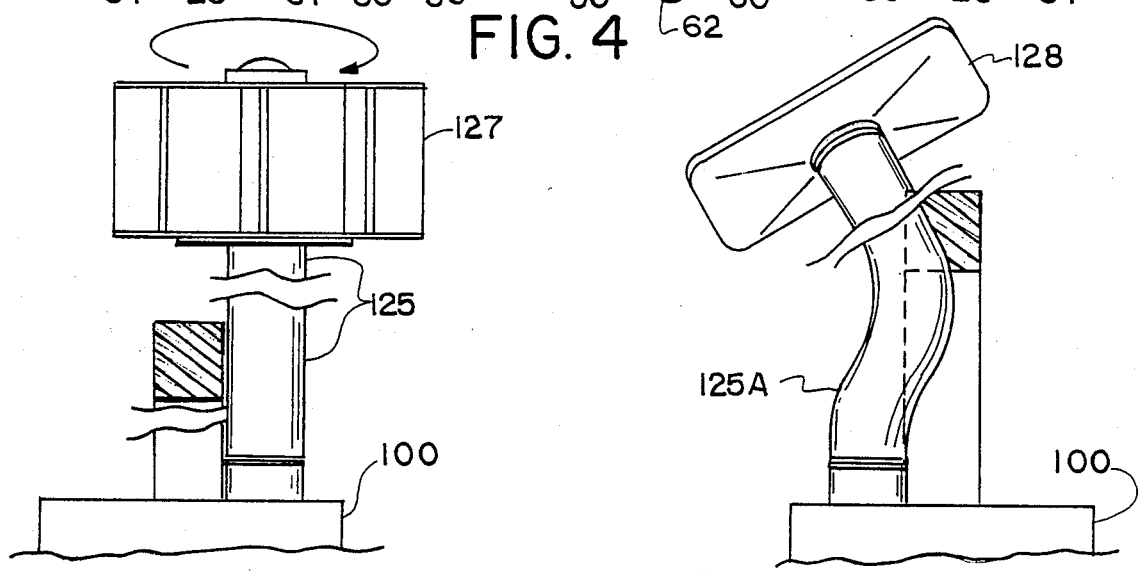
FIG. 5 shows a fragmented, end elevation view of control module 100 with air hose 140 and air distributor 150 attached.
FIG. 6 shows a fragmented, end elevation view of an alternate embodiment of control module 100.
Figure 7:
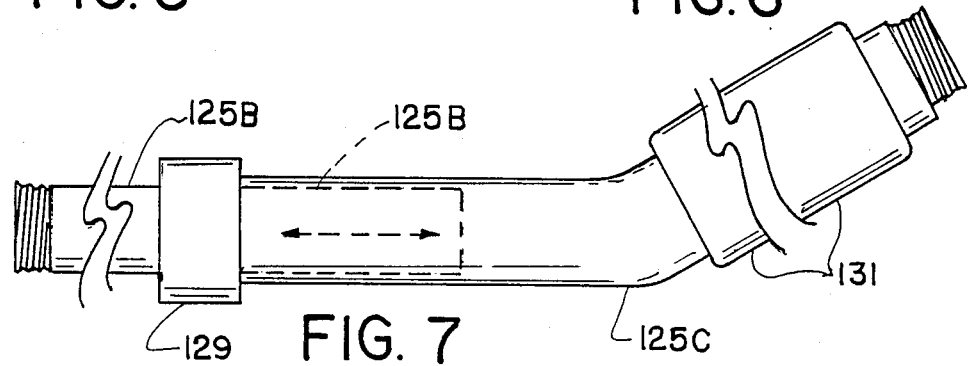
FIG. 7 shows an elevational view of a wand/handle attachment for module 100.

FIG. 1 shows an expanded, perspective view of the lightweight and portable Germicidal Ultraviolet Lamp 10. Lamp 10, in FIG. 1, has been expanded into three components or modules, for ease of description only, as follows: a base module 20, a Power module 70 and a control module 100. As shown by the arrows in FIG. 1, control module 100 fits inside the top of power module 70 (as will be explained) and both of those modules sit on top of base module 20, and are latched thereto as at the ends thereof to form the housing for lamp 10. FIGS. 5, 6 and 7 show elevational views of wand 125 attached to control module 100.

Figure 3:
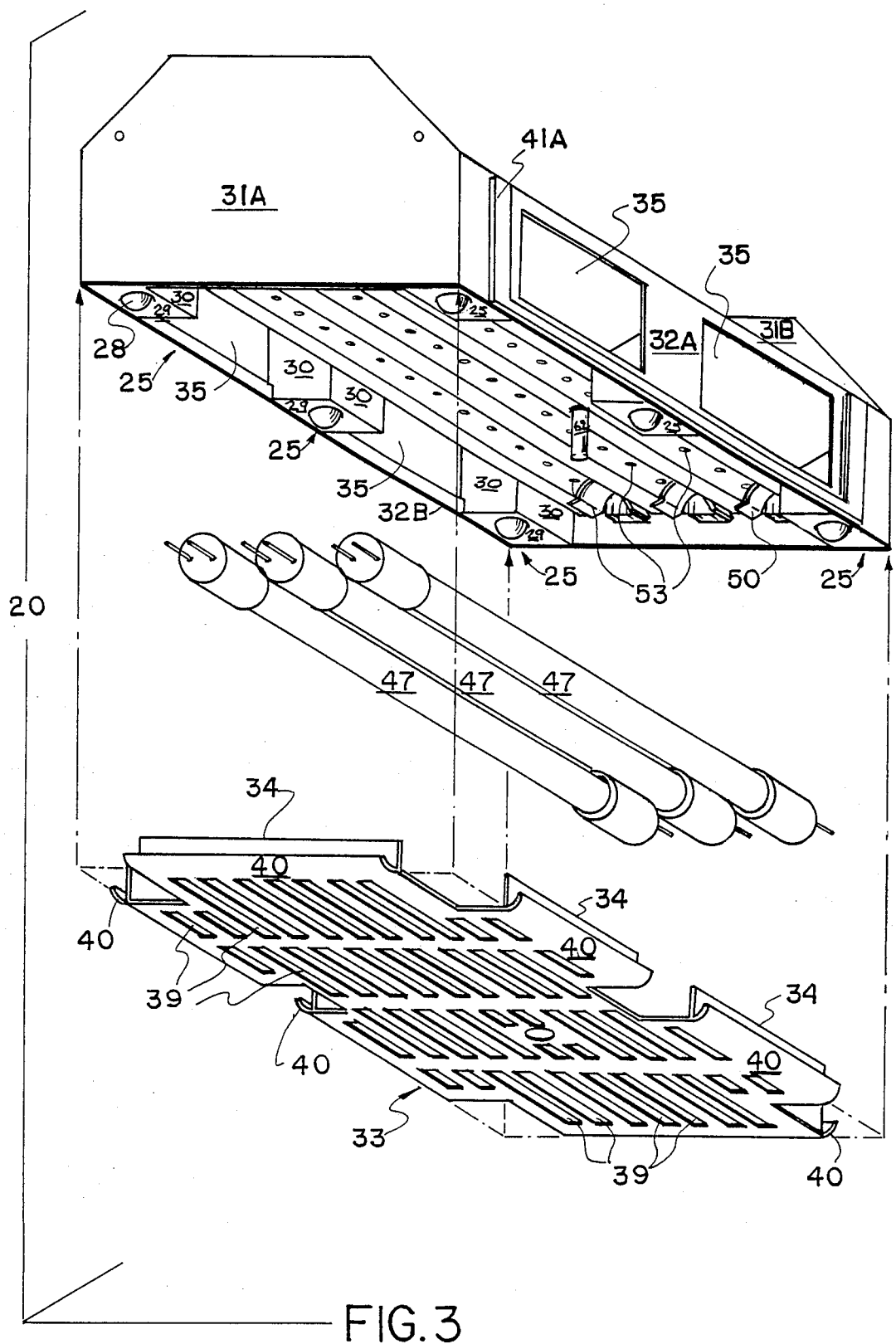
FIG. 3 shows an expanded perspective view of base module 20 as seen from the underside thereof and with louvered filters, 45 removed.
Figure 4:
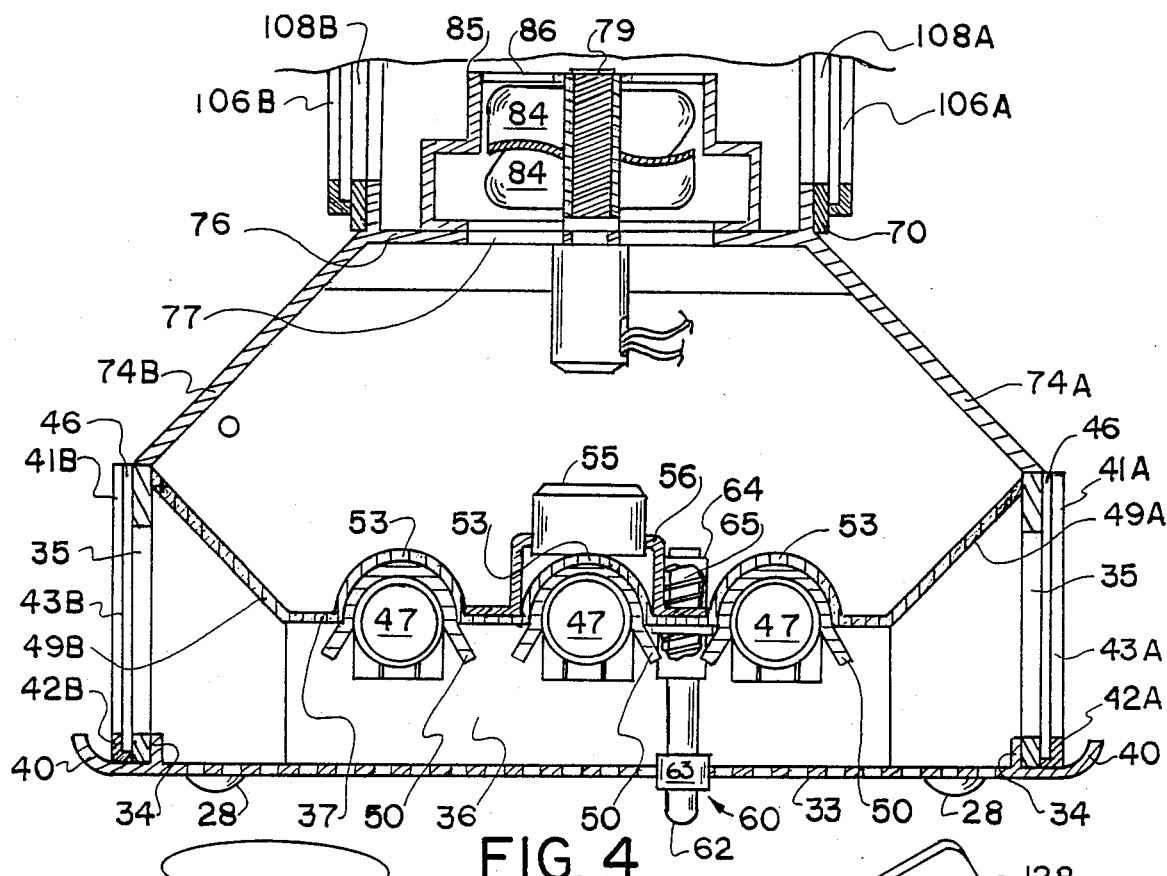
FIG. 4 shows a partial cross-sectional view of lamp 10 taken along lines IV—IV of FIG. 1.

Base module 20, as shown in an expanded perspective view in FIG. 3, is made of two parallel end pieces 31A, 31B fixedly joined at each side thereof to parallel side pieces 32A, 32B (32B not shown in FIG. 1) as is known in the industry. End .pPieces 31A, 31B and side pieces 32A, 32B are made of any lightweight, molded plastic material that is known to be strong and easily cleaned. FIG. 4 shows a partial cross-sectional view of base module 20 and power module 70 taken along lines IV—IV of FIG. 3. Side pieces 32A, 32B have openings 35 of predetermined size cut therein to allow air to flow through a filter into light chamber 36 and reflected UV light from a plurality of tubes 47 (as will be described) to shine out thereof, thus effectively killing any germs on adjacent surfaces (such as walls). Chamber 36 is formed by the inside surfaces of end pieces 31A, 31B and side pieces 32A, 32B and a light reflecting partition 37 (as will be explained below). There are a plurality of movement means 25, six being shown in FIG. 3, attached to the inside surfaces of both end pieces 31A, 31B and side pieces 32A, 32B near the bottom edges thereof. FIG. 2 shows a fragmentary end elevation of means 25 with end piece 31A cutaway, and, as seen in FIG. 3, means 25 (as will be further described below) are positioned in each corner of chamber 36 and midway along side pieces 32A, 32B to provide stable, ball-type rollers for lamp 10 to be moved around on. A grate 33 of predetermined length and width has fitting sections 34 (only three shown in FIG. 3) of predetermined height and width extending at a perpendicular angle therefrom and a plurality of slits 39, for a purpose to be described later, cut therein. Grate 33 with fitting sections 34 is made of lightweight molded plastic, as is known in the art, and snaps into a fitting arrangement at the bottom of chamber 36 by forcing individual fitting sections 34 inside aligned corresponding areas of end pieces 31A, 31B or side pieces 32A, 32B. Slits 39 are from ⅛ to ¼ inch wide and from ¾" to 1" long to prevent sizeable lightweight objects, found in a hospital, from passing from the outside into light chamber 36. An alternate embodiment thereto would use a section of fine mesh screen in place of grate 33.

Curved rails, or skids, 40 extend from predetermined positions on grate 33 to allow lamp 10 to slide over objects as it moves over a surface. Rails 40, as can be seen in FIG. 1, extend outwardly of end pieces 31A, 31B and side pieces 32A, 32B, and curl upwards and inwardly toward those pieces in an arc of approximately ¼ of a circle. Rails 40 also act as a bumper guard for lamp 10 and are of predetermined width to fit around, and be adjacent to, means 25, said means (as shown in FIG. 2) comprising a ball socket 26 set over a ball hole 27, of a smaller diameter than the circumference of a ball 28, in a plate 29, to rotatingly engage ball 28 trapped in said hole 27 by plate 29. Other forms of rollers or wheels may be employed to give mobility to lamp 10. Walls 30 are attached orthogonally with plate 29 to end pieces 31A, 31B and side pieces 32A, 32B, as the case may be, to form an enclosure for each means 25.

As seen in FIGS. 1 and 4, side pieces 32A, 32B have lower filter frame structures 41A, 41B affixed to the outside surfaces thereof in predetermined positions surrounding side piece openings 35. Structures 41A, 41B are identical and as can be seen clearly in FIG. 4, both structures have right-angle pieces 42A, 42B connecting side rails 43A, 43B to allow for proper spacing of structures 41A, 41B from side pieces 32A, 32B, respectively. A louvered filter 45 having fine mesh screening and adjustable fins 46 (see FIG. 2), that can either be angled to shield the UV light from eyesight or set horizontally (as known in the art) to allow UV light to shine out to surfaces and crevices alongside, and made using techniques known in the art, is placed into the opening between side piece 32A, 32B, and held in by, frame structure 41A, 42B, respectively.

Figures 9, 9A:
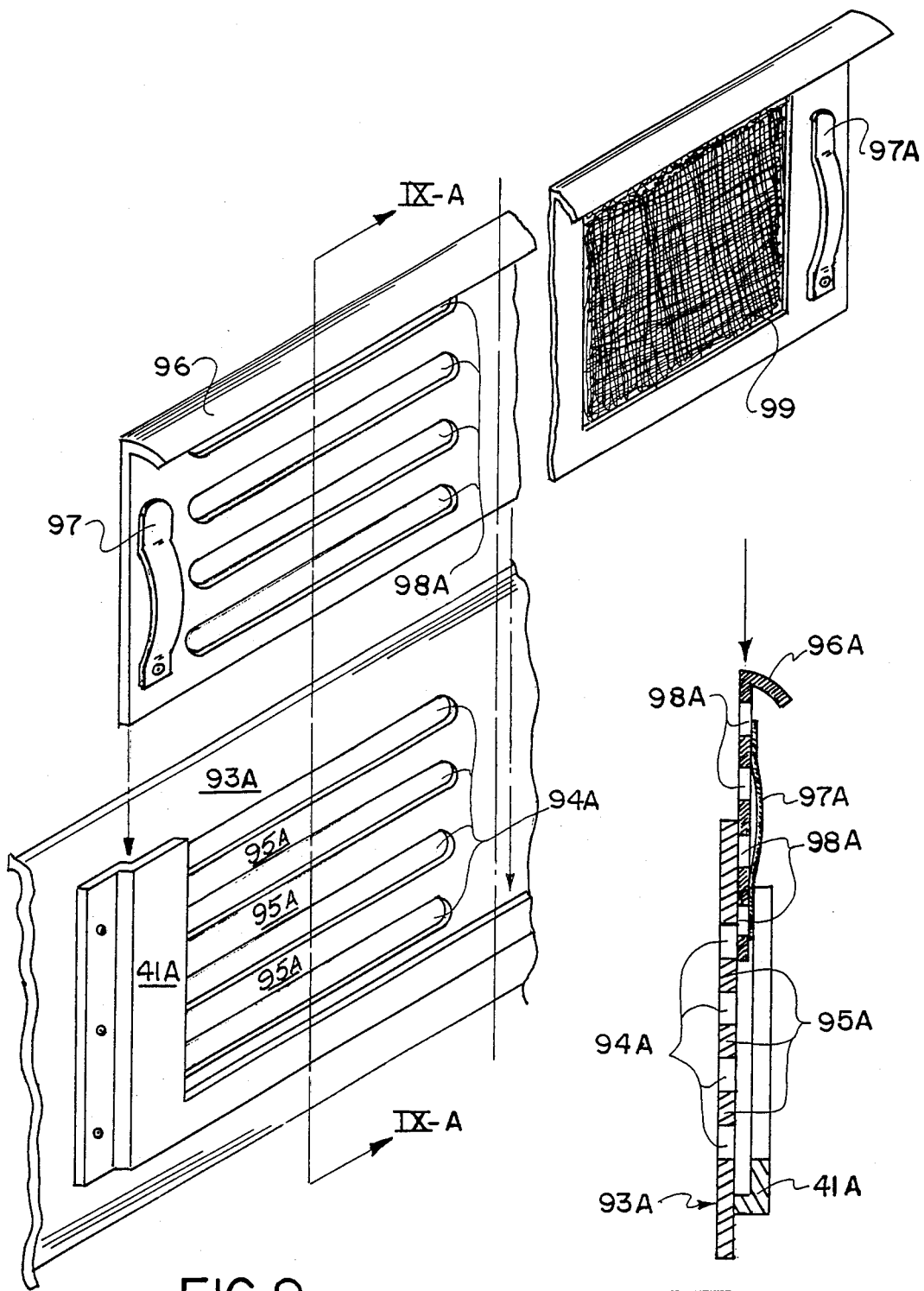
FIG. 9 shows a fragmentary, perspective view of an alternate embodiment at the side piece 93A of base module 20.
FIG. 9A shows a cross-sectional view of piece 93A taken along lines IXA—IXA of FIG. 9.

As seen in FIG. 4, light reflecting partition 37 is constructed to allow UV lights to set close to grate 33 and to allow both the full flow of air to enter chamber 36 through substantially the entire area of openings 35 and from around substantially all edges of pieces 31A, 31B, 32A and 32B, and to allow UV light to shine out through opening 35. (See FIGS. 9, 9A which show sliding frame 96 with slots 98A to open onto slots 94A in side piece 93A. Partition 37 is made from molded plastic and is coated with polished aluminum as is known in the industry. Partition 37 has a rectangular-shaped, reinforced mid-section 48 with oppositely-disposed, wing sections 49A, 49B extending at a predetermined incline therefrom. Wing sections 49A, 49B are substantially rectangular in shape and are conveniently made of a predetermined size to allow the outer edges thereof to be joined to the top edges of side pieces 32A, 32B, respectively, as is known in the industry. Mid-section 48 has a plurality of raised ridges (as looking at the top thereof) or semicircular indentations 52 (as looking up from underneath thereof) running substantially from end piece 31A to piece 31B. A plurality of air-flow holes 53 are drilled in each such indentation for a purpose to be described.

Each indentation 52 in mid-section 48 is constructed to act as both a semi-circular reflecting shield and an airflow guide for a Sterilamp, or other acceptable UV light, tube 47. Each such indentation 52 has a pair of tube clamps 50 fixed at opposite ends thereof (only one clamp for each indentation shown in FIG. 3) to securely grasp a tube 47 in an electrically connecting arrangement with the respective circline lampholder 51 (see FIG. 8).

Base module 20 has at leat one heat sensor 55 in the-form of a thermocouple, or other like device, set in a holder 56 that is positioned immediately above an air-flow hole 53 and fixed adjacent an indentation 52. Sensor 55 is connected into the electrical circuitry of lamp 10 (see FIG. 8) and detects both the warm-up temperature and an overheat temperature of tube 47. Thermostat 55 sends an appropriate signal to a buzzer 116 when a preset temperature, for example, showing that the light is operating at 70° F., is obtained. Additionally, a spring-biased safety override switch 60 is connected into the electrical circuitry of lamp 10 (see FIG. 8) to immediately shut off power to the device whenever it is allowed to tip or tilt more than a predetermined amount. As seen in FIG. 4, switch 60 has a freely moveable probe 62 aligned by circular guide 63 (in grate 33) and probe housing 64 into a verticle orientation. An expansion spring 65 is attached between a midpoint on probe 62 and the inside top of housing 64 and continually forces probe 62 to extend until stopped by the surface lamp 10 is resting on. The limit on the distance spring 65 may extend has been predetermined to correspond to a maximum tilting angle of lamp 10 of 15 degrees from the surface it is resting on. Once lamp 10 tilts more than 15 degrees off of that surface, probe 62, as forced by spring 65, closes two connections (not shown) as is known in the art and sends a shut-off signal to the power source (see FIG. 8).

A power module 70 is constructed to fit securely over the top of base module 20, as shown by the arrows in FIG. 1. Module 70 is constructed in two halves: upper half 71 and lower half 72. Lower half 72 provides framework and rigidity and is built from oppositely disposed, trapazoidally-shaped end pieces 73A, 73B joined at their respective sides thereof to the edges of side pieces 74A, 74B (74B not shown in FIG. 1) as is known in the art. As can be seen from FIG. 1, end pieces 73A, 73B are built in predetermined dimensions to matingly fit over and adjacent to the correspondingly shaped sections of end pieces 31A, 31B, and enable quick fasteners 75 on each piece 73A, 73B (only two shown) to secure module 70 to base module 20. A single plate 76 connects the top edges of top side pieces 74A, 74B and has an opening 77 (see FIG. 4) therein for fan 79, as will be described. Upper half 71 is constructed in the form of a tray and has end pieces 80A, 80B joined at their respective side edges to the edges of tray side pieces 82A, 82B as described above. Trapazoidal sections are removed from pieces 82A, 82B for a purpose to be described. Top half 71 is fixedly attached over plate 76, and all such end pieces and side pieces can be made from strong, molded plastic as is known.

The top half 71 provides a convenient receptacle for securing fan 79 over opening 77 so that airborne germs are pulled by the rotating fan blades 84 from outside the bottom and sides of lamp 10, into chamber 36, up past UV tubes 47, through airflow holes 53, up to and through opening 77. Fan 79 can conveniently be any small D.C. fan, such as the Rotron Model FL24A308, that gives proper air currents of sufficient speed past UV tubes 47 and has housing 85 with an exhaust opening 86 at the top thereof. If additional air currents are desired, a 3 inch, 110 VAC fan may be coupled into the circuitry. Top half 71 also provides a secure base for the lamp electronic circuitry 90 (see FIG. 8) and the required ballasts 92, such as Model 24 F 15 U from the Bodine Co., for tubes 47 as known in the art.

A control module 100 made, of predetermined dimensions, with oppositely disposed end pieces 101A, 101B joined at their side edges thereof to the side edges of oppositely disposed side pieces 102A, 102B and secured at the upper edges thereof by top section 103 is fitted over top half 71, as shown by the arrows and secured as a roof thereto by eight fasteners 75 (only four shown). All pieces are made of strong plastic, or other suitable material, and a convenient handle 105 is securely fixed to top section 103 to provide portability to lamp 10. As seen in FIGS. 1 and 4, pieces 102A, 102B each have upper filter frame structures 106 affixed to the outside surfaces thereof in predetermined positions surrounding respective side piece openings 108A, 108B (see FIG. 4). Structures 106A, 106B are identical to structures 41A, 41B. A louvered filter 109 with closeable fins 110, as is known in the art, is placed into structures 106A, 106B for a purpose to be described.

Control module 100 has a first rocker-type switch 112, as known in the art, located on top surface 103, connected to allow line current to flow through a power supply 130, such as a model #1040-4A1E from the Power General Company, into lamp 10 and a second rocker-type switch 114, adjacent the first switch, connected to override safety shut-off 60. In addition, a buzzer 115 is placed on top end piece 101A and connected to heat sensor 55, as will be explained. A two-position, spring-loaded on-off switch 116 is located adjacent buzzer switch 115 and connected to bypass buzzer 115 as will be explained (see FIG. 8).

Figure 8:
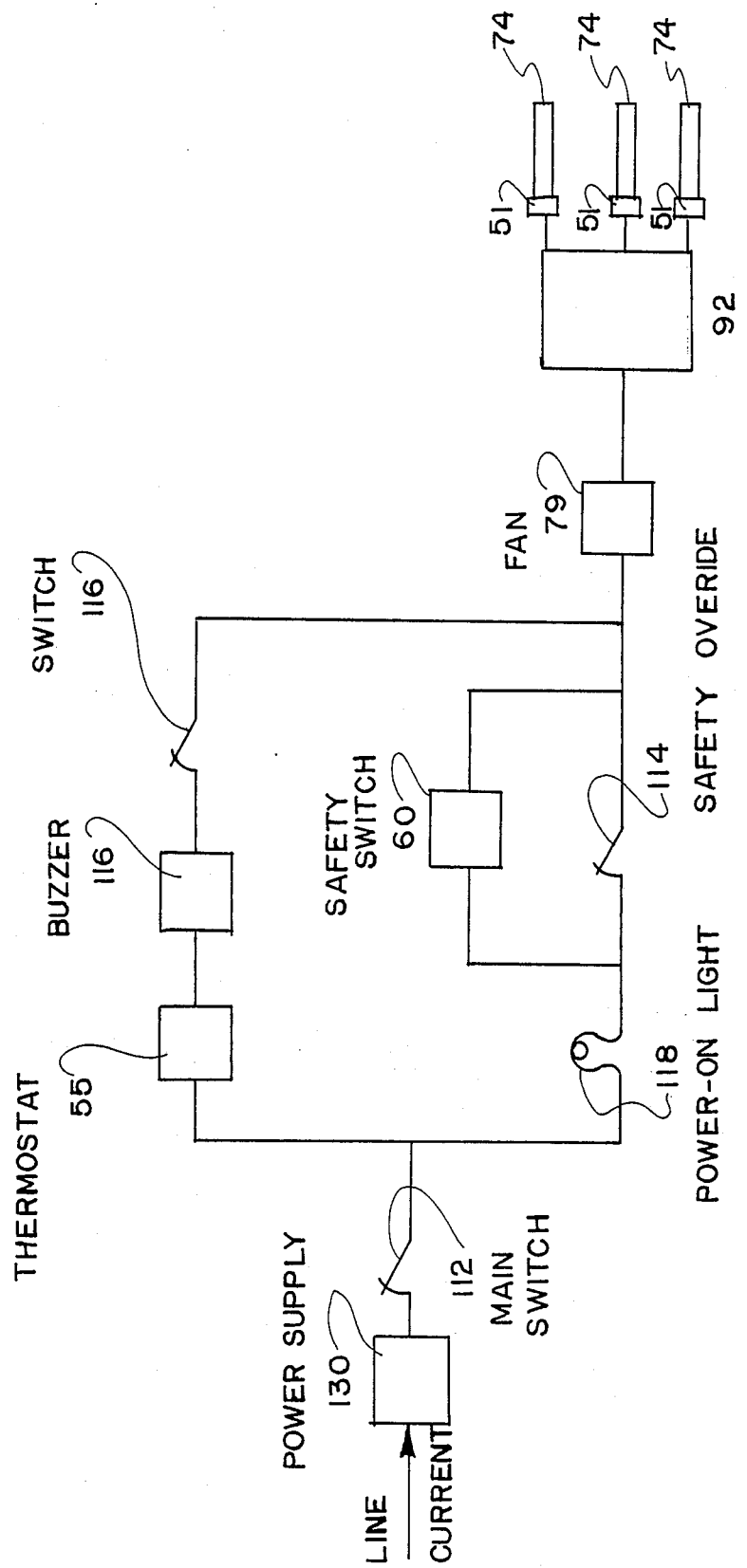
FIG. 8 shows a block diagram of electronic control circuitry 90.

The operation of lamp 10 will now be explained with reference to the schematic block diagram in FIG. 8. Line voltage enters into a power supply 130 and is converted to 24 volts and 1.7 amps by means well-known in the industry. Switch 112 activates the circuitry 90 and if either probe 62 is compressed or override switch 114 is depressed, power will flow to the remainder of circuit 90. This parallel connection allows a user of lamp 10 to pick the lamp 10 up off of the surface and continue current to tubes 47 even though probe 62 has extended sufficiently to close its power shut-off contacts (not shown), which would thereby disconnect the power from tubes 47. If switch 114 is activated to override safety switch 60, it should be reset once lamp 10 is placed on a level surface. As power is turned on by pressing switch 112, a power-on light 118 is illuminated.

Current flows to thermocouple 55, which switch will close and activate buzzer 115 when UV tubes 47 are operating at sufficient strength to kill germs. A buzzer switch 116, which is normally open, can be activated and used to open the circuit to buzzer 115 thereby silencing it. Lamp 10 is constructed so that there is a continual flow of air and airborn germ from around the edges of pieces 31A, 31B, 32A, 32B and up from the surface or from inside carpet fibers past tubes 47 to achieve the time-exposure to UV light to "kill" all the germs. The air and germs are pulled at a moderate rate from outside lamp 10 through filters 46 and near the bottom surface of grate 33 into light chamber 36 by fan 79. Chamber 36 is so designed so that either direct UV rays or reflected UV rays continually bathe the air immediately thereunder or alongside (in the case where fins 46 are set horizontally) of lamp 10. In a preferred embodiment, tubes 47 are as close to the surface as possible, preferably within ½ inch, for rapid killing of microorganisms. One hundred percent of the air flow is forced into chamber 36 and holes 53 allow only 75% to pass immediately adjacent one of the plurality of tubes 47 and out of the chamber, and the intensity of the UV wave and the time that it takes for air just entering chamber until it exits through one of the many air-flow holes 53 has been determined tokkill all of the airborne microorganisms carried therein. As lamp 10 is moved slowly over or alongside a particular surface at a predetermined speed, both the direct and the reflected UV rays coming from tubes 47 effectively kill any bacteria on said surface.

As seen in FIGS. 5, 6 and 7, lamp 10 has alternate means of flushing micro-organisms from behind objects or off of higher-level surfaces so that they may be carried into chamber 36. In a self-directing mode, fins 110 on louvered filter 109 are placed in the closed position, thereby forcing the flow of air caused by fan 79 to exit through roof nozzle 122 placed over a roof hole 121 (not shown) in top piece 103. Nozzle 122 is externally threaded and a hollow air-transport wand 125 with internal threads is connected thereto. As shown in FIG. 5, wand 125 can be rigid and support at the top end thereof a rotatable air flow distributor 127, as is known, or it can be flexible like a piece of hose 125A (see FIG. 6) and have a hand-held air flow director 128. In an alternate embodiment, the wand can be collapsible as at a twist-joint 129 to allow a smaller circumferenced section 125B (in phantom) to fit inside a larger circumferenced section 125C. A universal connector 131 can be fitted to the distil end of this wand 125C.

Obviously, many modifications and variations of the present invention are possible in light of the above teachings, and, it is therefor understood that within the scope of the disclosed inventive concept, the invention may be practiced otherwise than specifically described.

What I claim is:

1. A lightweight portable ultraviolet germicidal lamp to kill both airborn and surface carried bacteria, comprising:
   a housing structure having side walls, a top wall and an open lower end;
   a grid spanning, lengthwise and widthwise, the open lower end of said housing;
   support means at the lower end of said sidewalls to support the housing and permit easy movement thereof over a surface with the grid closely adjacent to said surface;
   a reflector closely spaced from and facing said grid, said reflector carried by said housing and spanning between opposite side walls thereof;
   a plurality of ultraviolet germicidal lamps intermediate said reflector and grid extending lengthwise of said housing and parallel to said lengthwise grid;
   means defining air openings in said reflector above said lamps;
   fan means at the top wall of said housing to draw air from adjacent said surface beneath the grid upwardly across said lamps and through the reflector air openings, and discharge the same upwardly through the top wall; and
   control circuitry carried by said housing including switch means to control operation of said fan and lamps.

2. Apparatus in accordance with claim 1 including handle means on the top wall of said housing to permit easy movement of said apparatus over a surface.

3. Apparatus in accordance with claim 1 wherein said switch means includes a first master switch to turn the lamps and fan on and off, and a second position sensitive switch to open the circuit to said lamps when said apparatus is moved out of engagement with said surface.

4. Apparatus in accordance with claim 3 in which said second switch extends downwardly below said grid in engagement with the surface supporting said apparatus, said second switch biased toward an open position to open the circuit to said lamps when moved out of engagement with said surface.

5. Apparatus in accordance with claim 3 including an override switch spring biased to an open position and manually depressible to complete a circuit to said lamps when said second switch is open.

6. Apparatus in accordance with claim 1 wherein said support means includes a plurality of rotatable balls partially recessed within said housing.

7. Apparatus in accordance with claim 6 wherein said support means further includes planar skid portions at the lower surface of said housing having outwardly and upwardly curved edge portions at opposite walls of said housing to permit said apparatus to ride over projections on the surface on which it is supported.

8. Apparatus in accordance with claim 1 including thermostatically operated signal means to emit a signal when said light source has come to full intensity.

9. Apparatus in accordance with claim 1 wherein said lamps are in the form of elongated tubes extending substantially the full length of said apparatus and spaced uniformly widthwise of said housing.

10. Apparatus in accordance with claim 9 in which said reflector is curved about the closely spaced from the upper portions of said tubes to cause the air and entrained bacteria drawn from said surface to flow around said tubes.

* * * * *

UNITED STATES PATENT AND TRADEMARK OFFICE
CERTIFICATE OF CORRECTION

PATENT NO. : 4,786,812

DATED : November 22, 1988

INVENTOR(S) : Wesley G. Humphreys

It is certified that error appears in the above-identified patent and that said Letters Patent is hereby corrected as shown below:

Column 8, line 30: change "the" to --and--

Signed and Sealed this

Twenty-first Day of March, 1989

*Attest:*

DONALD J. QUIGG

*Attesting Officer*   *Commissioner of Patents and Trademarks*